United States Patent [19]
Wiernicki et al.

[11] Patent Number: 5,503,538
[45] Date of Patent: Apr. 2, 1996

[54] INFUSION PUMP FOR MEDICINAL LIQUIDS

[75] Inventors: Michael V. Wiernicki, Trumansburg, N.Y.; Mark G. Scattergood, Broomfield, Colo.

[73] Assignee: Laboratoire Aguettant, Lyon, France

[21] Appl. No.: 290,834

[22] PCT Filed: Mar. 24, 1993

[86] PCT No.: PCT/FR93/00296

§ 371 Date: Sep. 14, 1994

§ 102(e) Date: Sep. 14, 1994

[87] PCT Pub. No.: WO93/18806

PCT Pub. Date: Sep. 30, 1993

[30] Foreign Application Priority Data

Mar. 24, 1992 [JP] Japan ................... 92 03775

[51] Int. Cl.⁶ .................................. A61M 5/142
[52] U.S. Cl. .......................... 417/560; 417/413.1
[58] Field of Search ................. 417/560, 531, 417/413.1

[56] References Cited

U.S. PATENT DOCUMENTS

| | | |
|---|---|---|
| 3,676,026 | 7/1972 | Tupper et al. . |
| 4,545,735 | 10/1985 | Ims ........................ 417/560 X |
| 4,573,888 | 3/1986 | Kitchin ...................... 417/560 |
| 4,646,781 | 3/1987 | McIntyre et al. ........... 417/560 X |
| 5,344,292 | 9/1994 | Rabenau .................. 417/413.1 |

FOREIGN PATENT DOCUMENTS

| | | |
|---|---|---|
| 480511 | 1/1952 | Canada ................... 417/560 |
| 1403779 | 11/1965 | France . |
| 3515624A1 | 11/1986 | Germany . |
| 8901972U1 | 6/1990 | Germany . |

Primary Examiner—Richard E. Gluck
Attorney, Agent, or Firm—Oliff & Berridge

[57] ABSTRACT

An infusion pump includes at least one cylinder-and-piston intake device for a liquid in a container and for dispensing the liquid into a connection link to the patient. In a preferred embodiment, the pump includes at least one metering cylinder containing a piston, each cylinder terminates in a cavity communicating with a supply receptacle for liquids, a diaphragm that is fluid-tight and deformable between the cylinder and the cavity, a disk located in each cavity, a spring urging the disk towards the cylinder, and a delivery connection between the cavity and the cylinder.

9 Claims, 4 Drawing Sheets

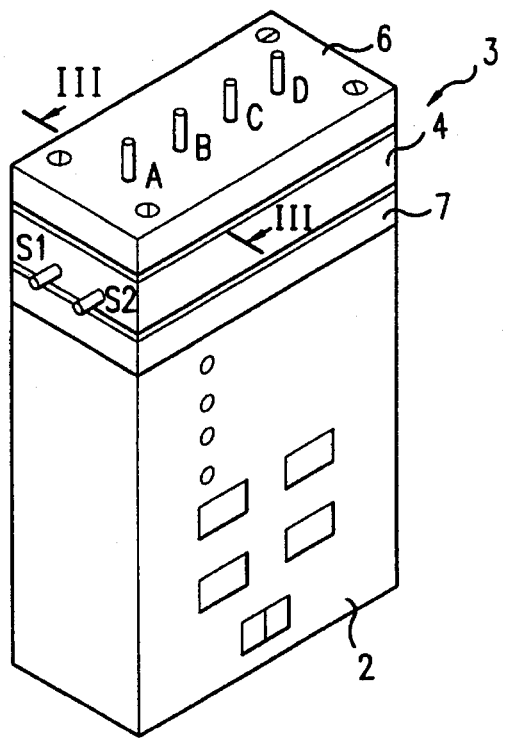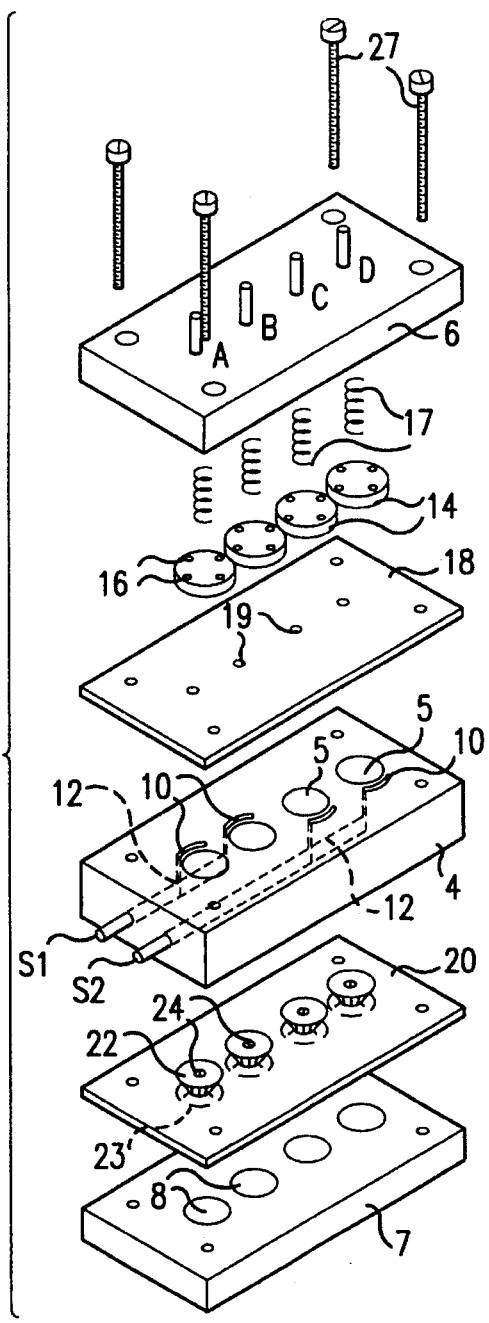

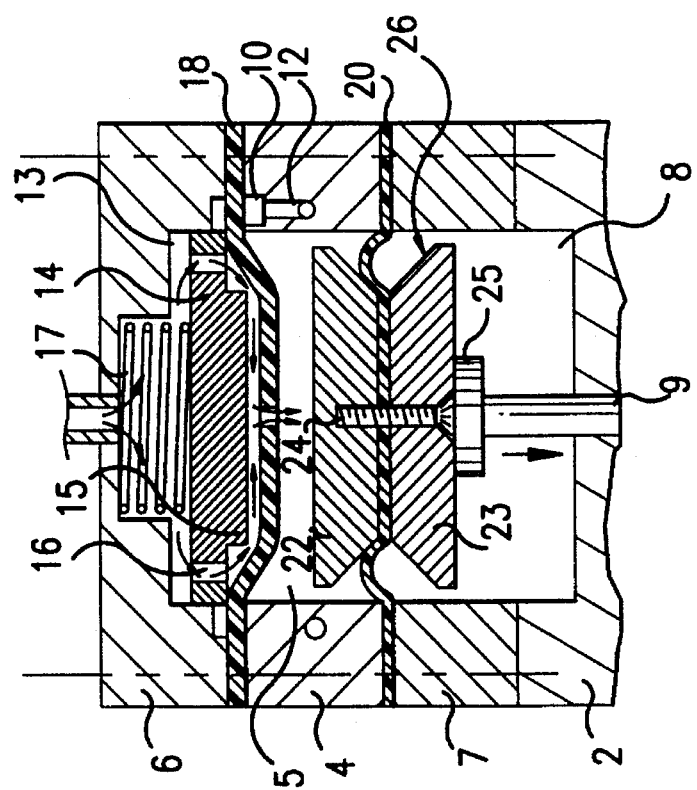
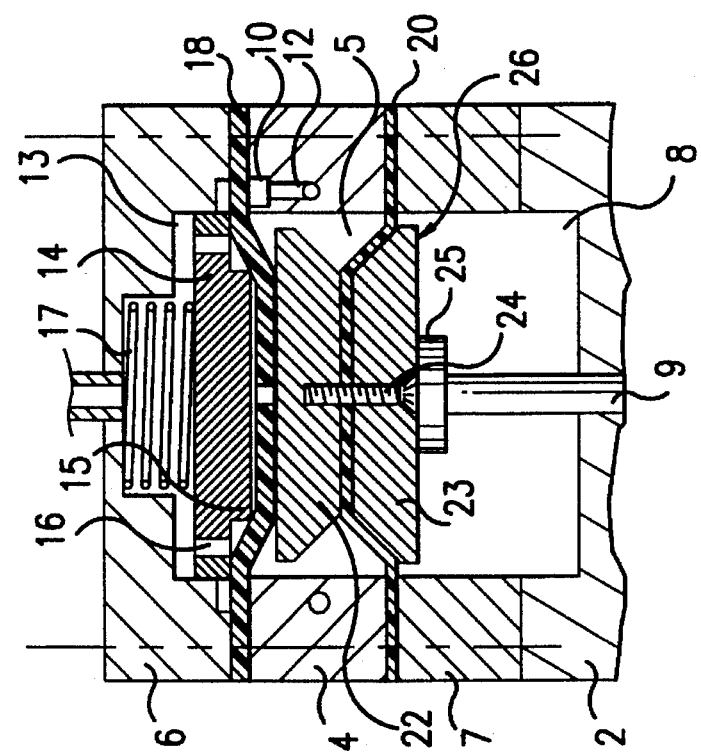

5,503,538

INFUSION PUMP FOR MEDICINAL LIQUIDS

The subject of the present invention is an infusion pump for medicinal liquids.

Intravenous infusion is an essential medication technique today in serious illnesses, cancer for example.

The efficacy of treatment is directly linked to the prescribed doses and limited by the level of toxicity of the active principles. The precision of the injection is therefore an important criterion in choosing the equipment to be used. In addition, it has been found that injection of an active principle, in order to respect the biological rhythms of the patient, must preferably be conducted at certain hours of the day, with the injection rate being variable throughout the injection period to take into account the immediate effects of the active principle on the organism.

It has also been found that it is possible, indeed advantageous, to combine a plurality of products, some of which can be injected simultaneously using the same catheter and others can be injected by different pathways.

There is a growing trend in modern medicine toward home treatment of the patient, and this is especially true for serious illnesses such as cancer and AIDS, which require a highly technological hospital setting and followup at the patient's home.

The infusion equipment now on the market does not take this trend toward home care into account. Existing portable pumps are generally heavy and cumbersome, and have limited autonomy. The pumps most often used are peristaltic pumps that squeeze a polymer or silicone tube to displace the product between a reservoir and the catheter supplying the patient.

This type of device suffers from the disadvantage of combining technical solutions with considerable size and weight:

Squeezing the tube requires a considerable force, produced by a system of rollers that is both cumbersome and heavy. The motor must be dimensioned to develop these squeezing forces, resulting in considerable weight. The power consumption of the motor is considerable, so that a number of disposable or rechargeable batteries that are both bulky and heavy is required, contradicting the idea of a portable pump.

Another solution consists in using devices of the syringe type in which the plunger of a syringe containing the product to be injected is driven stepwise by a motor. Apart from the disadvantages of weight and size described above, a system of this kind generally does not allow programming and can only be used for infusing a limited volume of liquid.

The goal of the invention is to provide an infusion pump for medicinal liquids with several channels, in other words one capable of allowing simultaneous infusion of several medicinal liquids with provision for mixing these liquids, or not, inside the pump, resulting in very limited size and reduced weight, while providing a very high degree of precision over a very wide throughput range, varying for example between 1 milliliter per day and 300 milliliters per hour, and offering considerable safety for the patient.

Another goal of the invention is to provide an infusion pump comprising a portion for transferring liquids, removably mounted on a housing for controlling and driving the pump.

To this end, the pump in question, of the type comprising at least one cylinder-and-piston device for drawing a liquid into a receptacle, and delivering the liquid to a connection linked to the patient, is characterized by comprising the following:

a first section containing at least one metering cylinder, containing a piston driven with an alternating motion, terminating at one face of the part, perpendicular to said face;

a second part abutting the face of the first part at which each cylinder terminates, having opposite each cylinder a cavity with a diameter larger than that of the corresponding cylinder, and communicating with a supply receptacle for liquid;

a fluid-tight, elastically deformable diaphragm clamped between the two parts, and having a hole opposite each cylinder;

a disk mounted in each cavity of the second part, with the face of said disk facing the first part being stepped and comprising an external part that abuts, through the diaphragm on the face of the first part in which the corresponding cylinder terminates, precisely around this cylinder, and a central part projecting from the interior of the cylinder, said disk comprising regularly distributed through holes provided near its periphery;

a spring urging the disk toward the first part; and associated with each cylinder, a hole terminating in the same face of the first part as the cylinder in question, said hole being associated with a vacuum connection provided in this part and located near the cylinder, opposite the same cavity as this cylinder, but beyond the disk containing this cavity, and covered by the diaphragm clamped between the two parts.

The pump according to the invention is one in which each liquid is metered by a piston-and-cylinder system. This system draws the liquid into the metering cylinder, then dispenses it from the latter into the supply line to the infusion catheter.

The originality of this pump resides essentially in the fact that the functions of the two check valves, located respectively upstream and downstream of the metering cylinder, are performed by the diaphragm located between the first and second parts.

When a piston moves in a direction that increases the volume of the metering cylinder, the vacuum created inside the metering cylinder is translated into a deformation of the diaphragm toward the center of the metering cylinder, permitting liquid to pass from the cavity provided in the second part, between the disk containing the latter and the diaphragm, and through the central opening of the diaphragm into the metering cylinder.

On the other hand, when the piston moves in a direction that reduces the volume of the metering cylinder, the pressure exerted by the liquid contained in this cylinder on the diaphragm, presses the latter tightly against the disk, while permitting deformation of the external part of the diaphragm to ensure communication of the cylinder with the adjacent hole, connected to a connection for delivery of the liquid.

It is possible to provide, in the first and second parts, a plurality of metering pumps, four for example, this embodiment being very simple in that the first and second parts can be constituted for example by parallelipipedic plates made of a synthetic material such as a polycarbonate.

It should be noted that depending on the application of the liquids carried by the different cylinder-and-piston assemblies forming part of a single pump, it is possible to provide inside the first part, delivery networks that may or may not communicate with one another. For this purpose it is sufficient to mold a first part suitable for the intended application.

In addition, this sandwich design makes it possible to incorporate in the delivery channels all manner of safety devices, including those for detecting air and overpressure. The delivery connections may be made in the first part, so that they terminate for their entire lengths at the face of the second part abutting said part, or on the contrary can be provided in the thickness of the first part, terminating in holes located adjacent to metering cylinders.

According to one characteristic of this pump the disk located in the cavity of the second part comprises a cylindrical part with a large diameter, extended in its central part and on the cylinder side by a cylindrical part with a diameter smaller than that of the cylinder, with through holes in the external part and terminating opposite the cylinder.

This stepped structure improves sealing, since the fit of the disk against the diaphragm is provided by a plurality of concentric ridges.

Advantageously, this pump comprises a third part, in contact with the first part and opposite the second part, said third part having bores extending the cylinders of the first part, with a sealing diaphragm being clamped between the first and third parts, and with the piston of each pump comprising two parts assembled together and located on either side of the sealing diaphragm, with the one located in the cylinder being made of a material compatible with the liquid to be transported and the other being designed for attachment of piston-driving means.

According to one embodiment, the part of the piston located on the side of the third part is made of a ferromagnetic material designed for attachment to the magnetized end of a drive rod for movement.

Making each piston in two parts makes it possible to dissociate the functions of the piston by assigning to the part located inside the metering cylinder, the function of drawing in and compressing the liquid contained in this cylinder, and by assigning to the part located on the other side of the diaphragm, the sole function of holding the piston-driving means.

It is therefore possible to use, for the part of the piston located outside the metering cylinder, a material that is not necessarily compatible with the liquid being transported, and which can be for example a ferromagnetic material allowing immediate and reversible locking of this part of the piston to the magnetized end of a drive rod for moving said piston.

The three parts and their intermediate diaphragms are assembled together and form an independent functional cassette designed to be removably installed in a control housing for driving the pistons.

Assembly can be conducted by screwing or by ultrasonic welding if the three parts are made of a synthetic material. These three parts form an independent functional cassette that must be sterilizable, especially by gamma radiation, and that can be mounted on a control housing driving the pistons, said housing containing, for each metering assembly, a motor, means for transmitting the movement of the motor to the piston, and possibly a programming device.

This control housing has a long service life, while the functional cassette is used only during a treatment. When the treatment is changed, medical personnel remove the used cassette and replace it in the control housing by a new cassette appropriate for the new treatment.

It is advantageous to provide keying means associated with the assembly means between the cassette and the housing, to ensure that the programmed treatment can be administered using the cassette that has just been mounted in the housing.

According to another characteristic of the invention, the two parts of the piston each have a section that tapers from its free end toward its end mounted on the other part.

The annular recess provided between the two parts opposite the piston accommodates the deformation movements of the diaphragm when the piston is displaced inside the metering chamber.

When the sealing diaphragm is made of a material that does not possess excellent flexibility, it is pre-shaped so that before it is installed, it has at the level of each piston a hollow part with a shape matching an inclined portion of a part of the piston and of the assembly zone of the two parts of the piston.

Consequently, the diaphragm has a tendency to tilt inside the metering cylinder between two equilibrium positions respectively corresponding to the retracted and advanced positions of the piston. The residual volume inside the piston can therefore be limited considerably.

In any event, the invention will be better understood from the following description with reference to the attached schematic diagram showing as nonlimiting examples a plurality of embodiments of the pump:

FIG. 1 is a perspective view of a pump designed to transport four separate liquids;

FIG. 2 is an exploded perspective view of various components of the functional cassette, ensuring the transfer of the liquid;

FIGS. 3 to 6 are four longitudinal sections of this cassette during four phases of its function;

Figure 4:
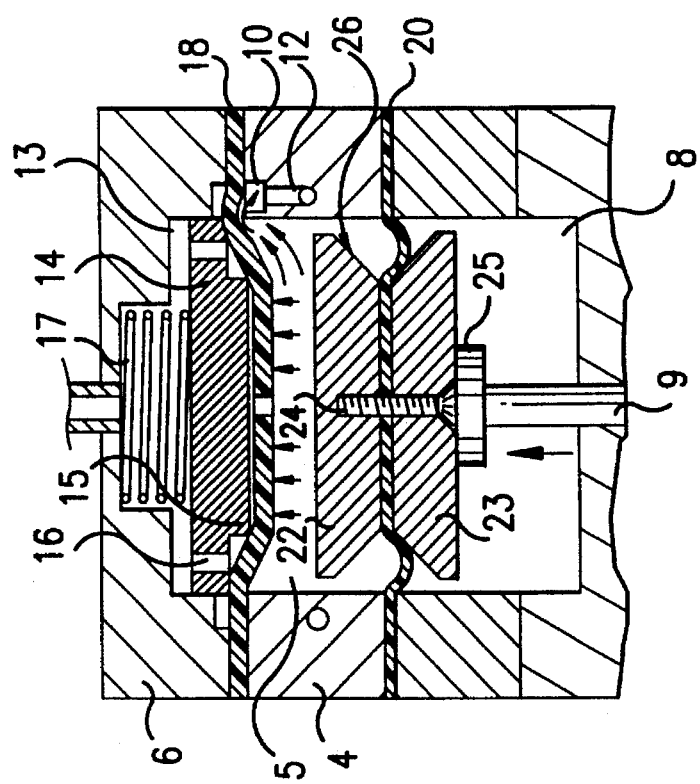

The infusion pump shown in FIG. 1 is designed to transport four separate liquids. It comprises a housing 2 containing means for programming the flow of each of the four liquids, and corresponding control of the pistons of the metering devices. This housing likewise contains electrical batteries to power the motors that displace the piston rods.

A cassette 3 is removably mounted on this housing, said cassette corresponding to the part that ensures the intake of each liquid into a receptacle constituted for example by a pouch made of synthetic material, a bottle with an air vent, or a syringe, and the delivery of this liquid into a connection linked by a catheter to the patient's body.

This cassette is constituted by a stack of three parallelipipedic parts, made of polycarbonate for example, namely a first central part 4 comprising four metering cylinders 5, a second part 6 provided with four connectors A, B, C, and D designed for connecting the four containers holding the liquids to be transferred, and a third part 7 with bores 8 corresponding to metering cylinders 5, and serving to allow the passage of piston-driving means to be described below, said driving means being shown in schematic form by rods 9 in the drawing.

In first part 4 there is likewise provided, adjacent to each metering cylinder 5, a hole 10 terminating at the face where it is assembled to second part 6. Each hole 10 is associated with a delivery connection 12, with connections 12 being arranged pairwise in the embodiment shown in FIG. 2, in such fashion that the metering cylinders that receive the liquids from connectors A and B have holes 10 located at an outlet S1, while input connectors C and D correspond to the metering cylinders and the holes whose connections 12 are arranged at an outlet S2.

It is likewise possible, in view of the very simple design of part 4, to provide it with devices to detect the passage of air or overpressure.

Figure 7:
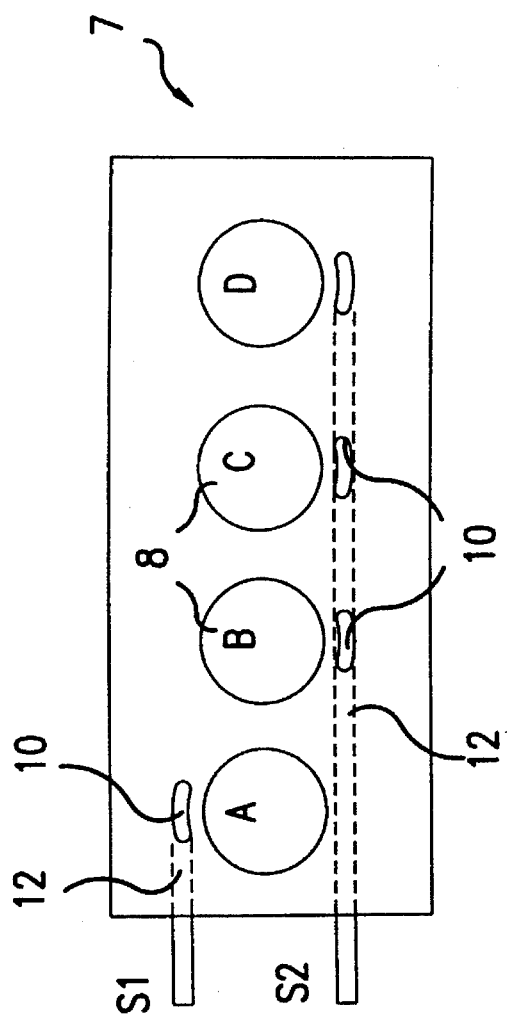
FIGS. 7 and 8 are two top views of two versions of the main and central parts of the cassette.
Figure 8:
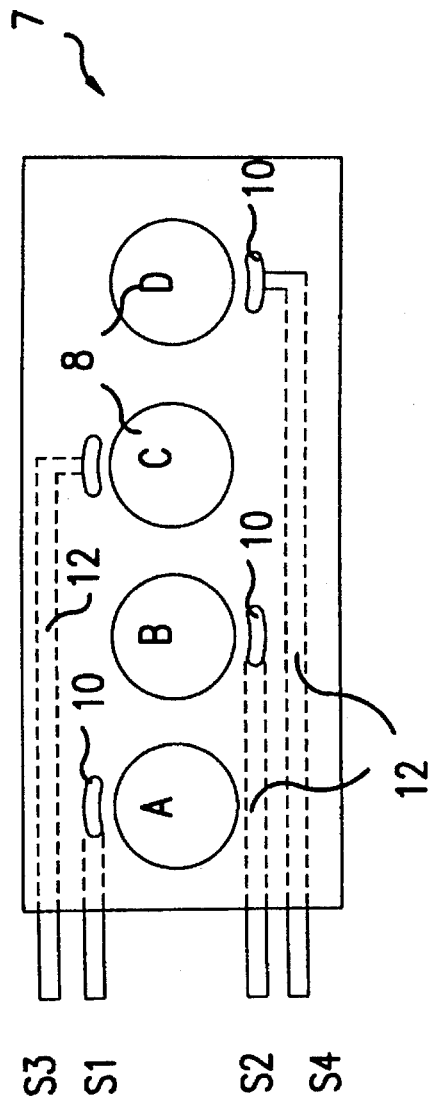

FIGS. 7 and 8 show embodiments of part 4 in which the connections between output connections 12 are different.

In the embodiment shown in FIG. 7, output connection S1 corresponds only to inlet A and outlet S2 resulting from the connection of the output connections corresponding to the liquids transported by connectors B, C, and D.

In FIG. 8, each of input connectors A, B, C, and D carries a specific liquid, and is associated with an output connection, S1, S2, S3, and S4, respectively.

Second part 6 comprises, opposite each metering cylinder 5, a cavity 13 with a diameter larger than that of corresponding cylinder 5, and communicating with a liquid supply container through one of connectors, A, B, C, and D, respectively. This cavity serves to accommodate a disk 14 whose face facing the metering cylinder is stepped. This cylinder comprises a part with a large diameter that can abut first part 4, beyond metering cylinder 5, extended in its central part and on the side of the metering cylinder by a cylindrical part 15 with a diameter smaller than that of the cylinder. Through holes 16, four of which are shown in FIG. 2, are provided in the external part of disk 14 and terminate opposite metering cylinder 5.

Disk 14 is subjected to the action of a spring 17 which urges it toward metering cylinder 5. Parts 4 and 6 are assembled by interposing a deformable diaphragm 18, made of polyethylene, polypropylene, or polytetrafluoroethylene for example. To avoid excessive compression of diaphragm 18 between parts 4 and 6, pins are provided between them to form spacing braces, not shown in the drawing, traversing diaphragm 18. In the part located opposite the center of each metering cylinder, diaphragm 8 has a hole 19.

Part 4 and third part 7 are assembled with interposition of a sealing diaphragm 20. Each metering cylinder 5 and corresponding bore 8 is associated with a piston connected to rod 9. This piston is made in two parts 22 and 23 assembled by a screw 24 for example, with part 22 inside metering chamber 5 and part 23 on the other side of sealing diaphragm 20, inside bore 8.

Part 22 of the piston is made of a material that is compatible with the liquid that will pass through the pump, while piston part 23 can be made of a material that is not compatible with such a liquid but possesses other qualities, such as allowing easy connection to drive rod 9.

Thus, piston part 23 can be made of a ferromagnetic material and drive rod 9 can be provided with a magnet 25 allowing instantaneous attachment and removal of the rod and piston, during assembly and disassembly of cassette 3 and housing 2, respectively.

As shown in FIGS. 3 to 6 in particular, the two piston parts 22 and 23 each have a section that tapers from its free end toward its end mounted on the other part, resulting in the provision of an annular recess 26, designed to facilitate deformation of sealing diaphragm 20 during piston displacement.

In this case as well, the sealing diaphragm can be made of polyethylene, polypropylene, polytetrafluoroethylene, polyester, or an elastomer-reinforced fabric. When diaphragm 20 does not possess perfect flexibility, it is advantageous to preshape it, giving it a shape that matches the profile of one of the sloping areas of the piston and of the assembly zone between the two piston parts.

The several parts 4, 6, and 7 with interposition of diaphragms 18 and 20 can be assembled by screwing for example, using a screw 27 in the embodiment shown in the drawing, noting that making parts 4, 6, and 7 of synthetic material allows them to be assembled by welding, for example by ultrasound.

FIGS. 3 to 6 show the operation of this pump, for one metering cylinder.

Figure 3:
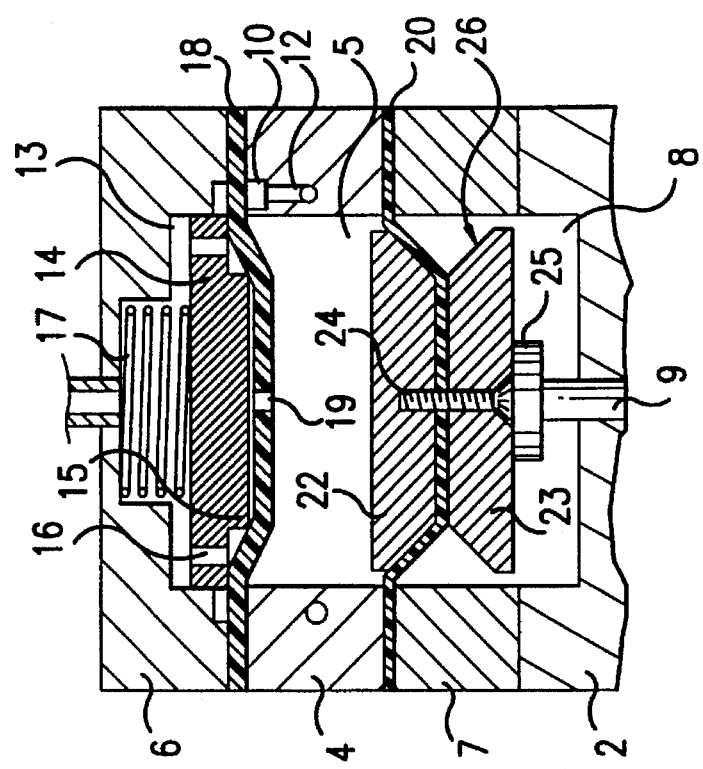

In the embodiment shown in FIG. 3, the piston is in the lower position, and metering cylinder 5 is filled with liquid.

When piston 22, 23 is displaced in a direction that reduces the volume of the cylinder, the pressure exerted by the liquid on the diaphragm presses the latter intimately against disk 14, preventing any passage of liquid from the chamber to the supply and also raising disk 14 partially against the action of spring 17, permitting sufficient deformation of the diaphragm to allow liquid to pass from metering cylinder 5 into matching hole 10, with the liquid being drained from this hole through connection 12. This phenomenon is illustrated by the arrows in FIG. 4.

FIG. 4 likewise illustrates the deformation of sealing diaphragm 20 during displacement of the piston and clearly shows that after the rounded deformation of FIG. 4, the diaphragm resumes, at the end of travel of the piston, a stable position as shown in FIG. 5 that is the reverse of the starting position corresponding to FIG. 3.

FIG. 5 shows the upper end of travel of the piston, and it is important to note that it corresponds to a very small dead space. When piston 22, 23 is driven in the opposite direction, a vacuum is created inside metering cylinder 5, causing deformation of the diaphragm toward the interior of this metering cylinder, ensuring separation of the diaphragm from central part 15 of disk 14, allowing liquid to pass from cavity 13, through through holes 16 between disk 14 and member 18, then through hole 19 in diaphragm 18, to fill metering cylinder 5. The movement shown in FIG. 6 continues back to the starting position shown in FIG. 3.

It is interesting to note that diaphragm 18 acts simultaneously as an inlet valve and an outlet valve for metering cylinder 5. Moreover, because of the presence of disk 14, the device offers every guarantee of safety in the event of overpressure at the inlet because this overpressure can in no way be translated into an increase in throughput that could be harmful to the patient.

Of course the invention provides a considerable improvement in the existing technology by providing an infusion pump, especially for outpatient treatment, very simple in design, highly reliable, and capable of modification to adapt to the type of treatment while retaining the same housing and the same structure for parts 6 and 7 at the end of the cassette by adapting central part 4, both as concerns its thickness to modify the volume of the metering chamber, and as concerns providing output ducts for grouping or not grouping the outlets for liquids to be infused.

Of course the invention is not limited to the embodiments of this pump described above as examples; on the contrary, it includes all variations thereon.

Thus, for example, it would be possible to regroup parts 4 and 7 and not to make a piston that has a perfect seal relative to the cylinder in a single part, without departing from the scope of the invention.

We claim:

1. An infusion pump for medicinal liquids, of the type comprising at least one cylinder-and-piston intake device for a liquid in a container and for dispensing the liquid into a connection linked to a patient, comprising;

a first part containing at least one metering cylinder, said at least one metering cylinder containing a piston driven with an alternating motion, terminating in a face of said first part, and perpendicular to said face;

a second part abutting the face of said first part in which said at least one metering cylinder terminates, said second part comprising, opposite each said at least one metering cylinder, at least one cavity with a diameter larger than a diameter of the corresponding said at least one metering cylinder and communicating with a container for supplying the liquid;

a diaphragm that is fluid-tight and elastically deformable, clamped between said first and second parts and comprising a hole opposite each of said at least one metering cylinder;

a disk fitted in each at least one cavity of said second part, a face of said disk facing said first part being stepped and comprising an outer part abutting, through the diaphragm, the face of the first part in which the corresponding at least one metering cylinder terminates, and a central part projecting from an interior of the at least one metering cylinder, said disk comprising plurality of disk holes arranged at regular intervals and provided near periphery of said disk;

a spring urging the disk toward the first part; and a plurality of cylinder holes terminating in the same face of said first part as the corresponding at least one metering cylinder, each hole of said plurality of cylinder holes being associated with a connection for delivery provided in said first part, said connection being located near said at least one metering cylinder and opposite the corresponding at least one cavity of said at least one metering cylinder, but beyond said disk containing said at least one cavity, and being covered by said diaphragm clamped between said first and second parts.

2. The pump according to claim 1, wherein said disk located in said at least one cavity of said second part comprises a cylindrical part with a diameter, extended at central disk part of said disk and on the side of the at least one metering cylinder by said central part with a diameter smaller than the diameter of said at least one metering cylinder, with said plurality of disk holes being provided in the external part and terminating opposite said corresponding at least one metering cylinder.

3. The pump according to claim 1, comprising a third part in contact with said first part opposite said second part, and said third part comprising a plurality of bores extending said at least one metering cylinder of the first part, a sealing diaphragm being clamped between said first and third parts, piston comprising a first and second piston part assembled to one another and located on either side of aid sealing diaphragm, said first piston part being made of a material compatible with the liquid to be transported and said second piston part (23) being designed for attachment of a piston-driving means for driving said piston.

4. The pump according to claim 3, said second piston part of the piston being made of a ferromagnetic material and designed for attachment to magnetized end of a rod for driving movement.

5. The pump according to claim 3, wherein said first and second piston part each have a section tapering from its free end toward its end mounted on the other part.

6. The pump according to claim 5, wherein said sealing diaphragm is preshaped so that, prior to assembly, said piston further comprises a hollow part with a profile corresponding to an inclined part of the piston and of the assembly zone of the first and second piston parts.

7. The pump according to claim 1, further comprising a plurality of braces forming spacers between said first and second parts for controlling the compression of the diaphragm.

8. The pump according to claim 3, wherein said first, second, and third parts and said corresponding diaphragms are assembled together to form an independent functional cassette configured to be installed removably on a housing for controlling and driving the piston.

9. The pump according to claim 8, further comprising keying elements associated with means for assembling the housing and the cassette containing the at least one metering cylinder.

* * * * *

UNITED STATES PATENT AND TRADEMARK OFFICE
CERTIFICATE OF CORRECTION

PATENT NO. : 5,503,538
DATED : April 2, 1996
INVENTOR(S) : Michael V. WIERNICKI and Mark G. SCATTERGOOD It is certified that error appears in the above-indentified patent and that said Letters Patent is hereby corrected as shown below:

On title page, item [73], please change Assignee name from "LABORATOIRE AGUETTANT" to --COMPAGNIE DE DEVELOPPEMENT AGUETTANT--.

Signed and Sealed this

Twenty-second Day of October, 1996

Attest:

BRUCE LEHMAN

Attesting Officer

Commissioner of Patents and Trademarks